United States Patent
Li

(10) Patent No.: US 6,727,495 B2
(45) Date of Patent: Apr. 27, 2004

(54) ION MOBILITY SPECTROMETER WITH HIGH ION TRANSMISSION EFFICIENCY

(75) Inventor: Gangqiang Li, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 5 days.

(21) Appl. No.: 10/053,077

(22) Filed: Jan. 17, 2002

(65) Prior Publication Data

US 2003/0132379 A1 Jul. 17, 2003

(51) Int. Cl.[7] ............................................... H01J 49/40
(52) U.S. Cl. ..................... 250/286; 250/281; 250/282; 250/286; 250/287; 250/280; 250/292
(58) Field of Search ............................ 250/286, 281, 250/282, 287, 280, 292

(56) References Cited

U.S. PATENT DOCUMENTS

| | | |
|---|---|---|
| 3,935,452 A | 1/1976 | Prince |
| 4,855,595 A | 8/1989 | Blanchard |
| 5,140,158 A | 8/1992 | Post |
| 5,280,175 A * | 1/1994 | Karl ........................... 250/287 |
| 5,523,659 A | 6/1996 | Swenson |
| 5,796,099 A | 8/1998 | Jackson |
| 5,869,344 A | 2/1999 | Linforth et al. |
| 5,905,258 A | 5/1999 | Clemmer et al. |
| 6,107,624 A | 8/2000 | Döring et al. |
| 6,107,628 A * | 8/2000 | Smith et al. ................ 250/292 |
| 6,111,250 A | 8/2000 | Thomson et al. |
| 2001/0032929 A1 | 10/2001 | Fuhrer et al. |

FOREIGN PATENT DOCUMENTS

WO     WO 01/65589    9/2001

OTHER PUBLICATIONS

Pub. No: US 2002/0070338A1, "Ion Mobility Spectrometer . . ." by Alexander V. Loboda. Pub. date: Jun. 13, 2002.*
Dieter Gerlich, "Inhomogeneous RF Fields: A Versatile Tool for the Study of Processes with Slow Ions", Advances in Chemical Physics Series, 1992, vol. 82, pp. 1–76.
Shenheng Guan et al., "Stacked-Ring Electrostatic Ion Guide",American Society for Mass Spectrometry, 1996, vol. 7, pp. 101–106.
Chris M. Lock et al., "Characterisation of High Pressure Quadrupole Collision Cells Possessing Direct Current Axial Fields", Rapid Communications in Mass Spectrometry, vol. 13, 1999, pp. 432–448.
Scott A. Shaffer et al. "Characterization of an Improved Electrodynamic Ion Funnel Interface for Electrospray Ionization Mass Spectrometry", Analytical Chemistry, vol. 71, No. 15, Aug. 1, 1999, pp. 2957–2964.
Gillig et al. "Periodic Field Focusing Ion Mobility Spectrometer" U.S. publication No. US2001/0032930A1, Pub. Date Oct. 25, 2001EV333999628US.

* cited by examiner

Primary Examiner—John R. Lee
Assistant Examiner—Zia R. Hashmi

(57) ABSTRACT

An ion mobility spectrometer comprising a drift tube having a central axis, along which a plurality of ring electrodes are arranged is provided. The plurality of ring electrodes provides a linear potential gradient along the central axis of the drift tube. In addition an RF voltage source coupled to the plurality of ring electrodes generates an oscillating RF potential within the internal region of each of the ring electrodes. The oscillating RF potential influences radial motion of the ions within the drift tube so that the ions remain within a radial space defined by the internal regions of the electrodes.

25 Claims, 6 Drawing Sheets

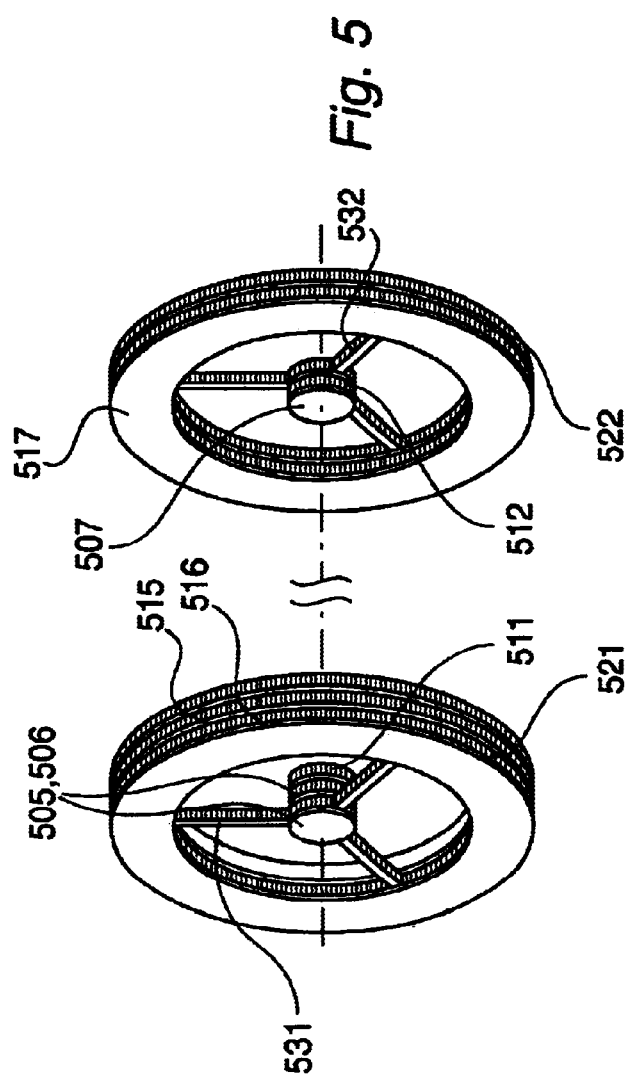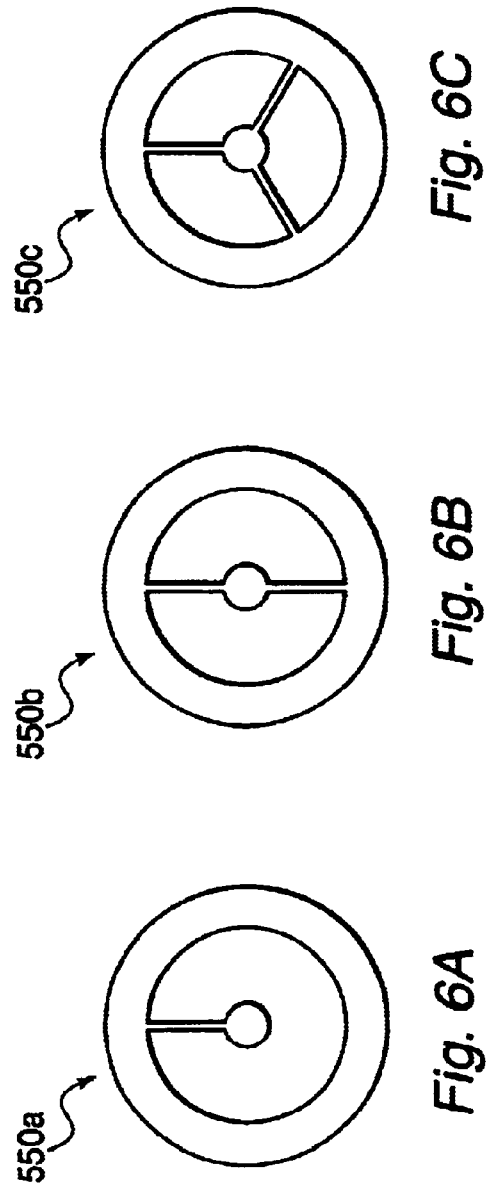

ION MOBILITY SPECTROMETER WITH HIGH ION TRANSMISSION EFFICIENCY

FIELD OF THE INVENTION

The present invention relates to mass spectroscopy systems, and more particularly, but without limitation, relates to an ion mobility spectrometer system that transmits ions through a drift tube to a collector with a high degree of efficiency.

BACKGROUND INFORMATION

Ion mobility spectrometers (IMS) differentiate between component molecules in a sample on the basis of the time taken by the component molecules, when ionized, to move through the length of a drift tube containing a drift gas under the influence of an electric field. A typical example of such an ion mobility spectrometer, shown in cross-section in FIG. 1, illustrates this mechanism. Molecules in a sample are ionized in a gaseous phase at an ion source 5, which may be, for example, a radioactive β-emitter, a photoionizer, or a corona-discharge arrangement. The ions generated at the source are then directed into the opening 11 at a first end of the drift tube 10. Within the drift tube 10, a series of ring-shaped electrodes (e.g., electrodes 15, 16) are arranged coaxially and are equally spaced throughout the length of the tube. The ring electrodes 15, 16 are electrically isolated and connected via resistors (e.g., 35, 36) to a voltage divider 40. A d.c. power supply 45 is coupled to the voltage divider 40, whereby the ring electrodes 15, 16 establish a linear potential gradient, typically in the range of 200 V/cm, along the central axis of the drift tube 10 which causes ions within the drift tube to move through the tube in a generally axial direction.

The drift tube 10 is filled with a drift gas, such as helium or nitrogen, at approximately atmospheric temperature and pressure, supplied through a drift gas inlet 21 at the opposite end of the drift tube. Collisions between the ions and drift gas molecules cause the ions to lose kinetic energy. In a steady state, the loss in kinetic energy is balanced by energy gained from the electric field. An equilibrium condition results in which the ions travel in the drift tube at a constant velocity given by:

$$v = KE \quad (1)$$

where K is referred to as the ion mobility constant and E is the axial electric field applied in the drift tube. According to current theoretical models (see Eiceman et al., *Ion Mobility Spectroscopy*, CRC Press 1993 pgs. 57–86), the mobility constant of a particular ion (at constant temperature and pressure) is related to the reduced mass of the ion and to a diffusion collision integral, which is related to the size and shape of the ion.

During operation, an ion gate electrode 50, usually consisting of a grid mesh mounted perpendicularly to the axis toward the first end of the drift tube 10, acts as a gatekeeper allowing packets of ions, typically several microseconds to several milliseconds in duration, to pass through when an electric pulse is applied to the gate. A collector electrode 60 is placed at the opposite end of the drift tube 10. As ion packets released from the gate 50 drift toward the collector 60, the ions within the packet are separated according to their various ion mobility constants. By measuring the travel times of the ions between the gate and the collector, their respective ion mobility constants can be readily calculated, and their specific masses and shapes can be deduced therefrom.

One of the factors that reduces optimal performance of such conventional IMS instruments is their generally low transmission efficiency due to radial migration of the ions in the drift chamber. This radial migration, mainly caused by initial divergence of the ion beam due to temperature gradients, transverse diffusion of the ions, and space charge repulsion between the ions, results in a large portion of the ions leaving the axial trajectory toward the ring electrodes 15, 16 where they become neutralized on contact. Such losses increase in proportion to the length of the drift tube as the ions have more time to become diverted from an axial trajectory. Thus, even though the resolution capabilities of IMS instruments provide for detecting sample concentrations as low several parts per trillion, their performance suffers because of the low transmission efficiencies, which can be as low as 1%.

What is therefore needed is a means of increasing the ion transmission efficiencies of IMS instruments by reducing radial ion diffusion in the drift tube, without sacrificing the high resolution and other advantageous qualities of these instruments.

SUMMARY OF THE INVENTION

The present invention provides an ion mobility spectrometer comprising a drift tube having a central axis along which a plurality of ring electrodes is arranged. The plurality of ring electrodes provide a linear potential gradient along the central axis of the drift tube. In addition, an RF voltage source, coupled to the plurality of ring electrodes, generates an oscillating RF potential within the internal region of each of the ring electrodes. The oscillating RF potential influences radial motion of the ions within the drift tube so that the ions remain within a radial space defined by the internal regions of the electrodes.

In one embodiment of the ion mobility spectrometer according to the present invention, each of the plurality of ring electrodes includes an even number of segments, wherein each segment is electrically insulated, and is maintained at an oscillating RF potential of an opposite polarity from adjacent segments. A multipole electric field is thereby generated within the respective internal region of each of the ring electrodes.

According to another embodiment, the ion mobility spectrometer according to the present invention includes a plurality of disk electrodes. Each of the plurality of disk electrodes is centered in the internal region of one of the plurality of ring electrodes, with each disk being coaxial with the drift tube. The RF voltage source is coupled to each of the plurality of disk electrodes such that an oscillating RF potential is generated between each of the plurality of ring electrodes and the respective disk electrode centered in the ring electrode.

The present invention also provides a method for efficiently transmitting ions along a linear trajectory in an ion mobility spectrometer. Ions are introduced into a cylindrical drift tube having a central axis. A plurality of ring electrodes are arranged in a stack along the central axis of the drift tube, each of the ring electrodes having an internal region perpendicular to the central axis of the drift tube. A linear potential gradient is generated along a central axis of the drift tube to influence motion of ions along the central axis, and an oscillating RF potential is generated within the internal region of each of the axially stacked ring electrodes that constrains radial motion of the ions perpendicular to the axis of stacked ring electrodes by influence of the oscillating RF potential.

BRIEF DESCRIPTION OF THE DRAWINGS

FIG. 5 is a perspective view depicting an embodiment for mounting the disk-shaped electrodes along the axis of an ion mobility spectrometer.

FIG. 6A depicts an integrated insulator having a ring portion, a disk portion and a single connecting spoke.

FIG. 6B depicts an integrated insulator having a ring portion, a disk portion and a two connecting spokes.

FIG. 6C depicts an integrated insulator having a ring portion, a disk portion and three connecting spokes.

DETAILED DESCRIPTION

In accordance with the present invention, oscillating radial RF fields are generated in the internal, central regions of the ring electrodes within the drift tube. The oscillating RF fields prevent radial diffusion of ions located within these internal regions through their time-varying alternating action, but do not interfere with the action of the linear potential along the axis of the drift tube, so that ion mobility in the axial direction is not affected. The radial oscillating fields influence the ions equally in all lateral directions, with the net effect that they are forced to remain inside the internal region without reaching the ring electrodes.

According to one embodiment, the ring electrodes are divided and separated into an even number of segments. Radio frequency voltages of opposite polarities, $+V \cos(\omega t)$ and $-V \cos(\omega t)$, respectively, are applied to adjacent pairs of segments, generating a radial RF field within the internal region of the segments. The radial field is characterized by the number of segments: quadrupole for four segments, hexapole for six segments, etc. For each of these multipole fields, the radial potential gradient varies according the RF frequency applied.

According to another embodiment, the ring electrodes are not segmented, but rather, disk-shaped electrodes are placed in the center of the ring electrodes. The ring electrodes and the disk electrodes receive RF frequency voltages of opposite polarity, generating an oscillating radial RF field in the internal region between the disks and the ring electrodes.

Figure 1:
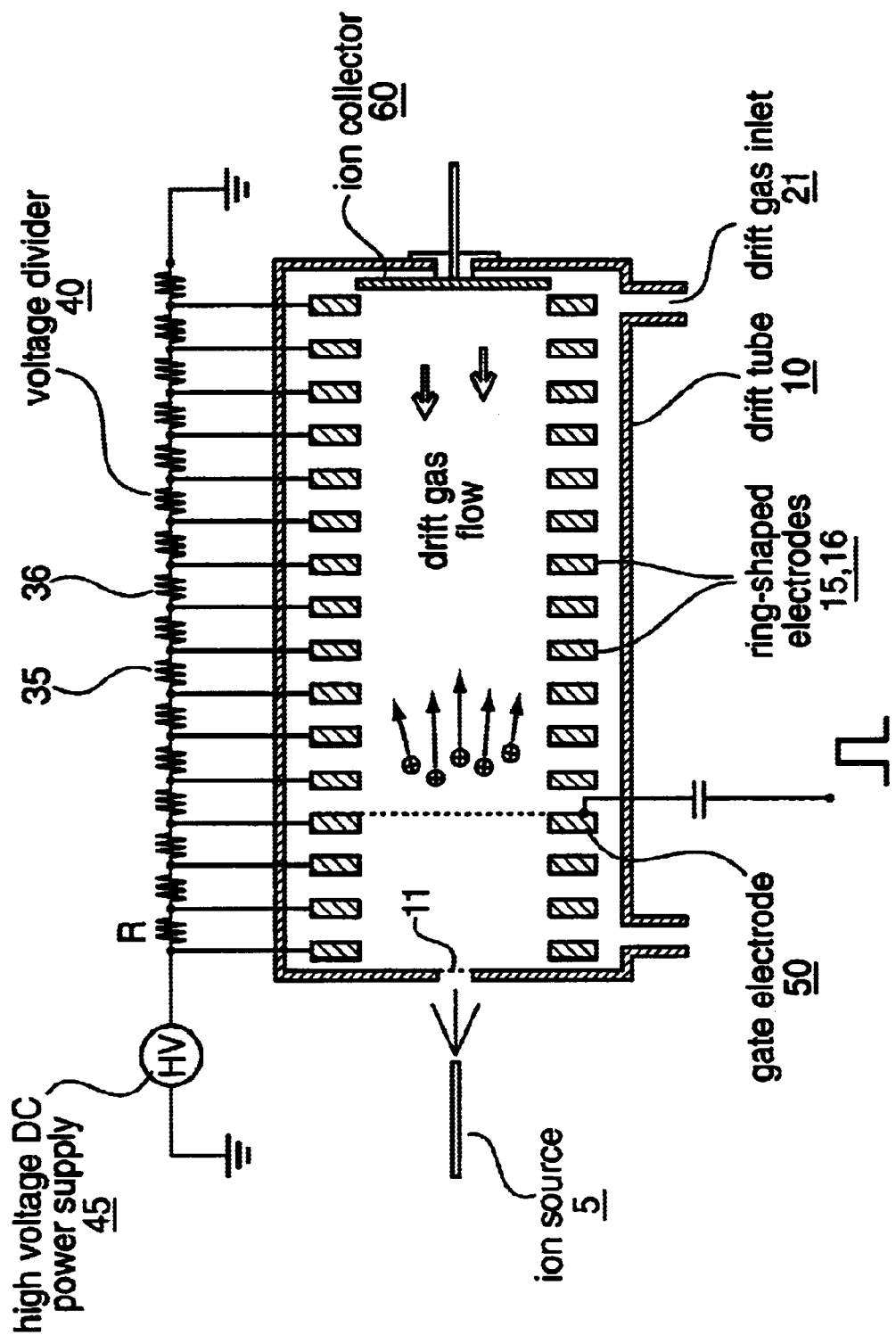
FIG. 1 shows a cross-section of a conventional ion mobility spectrometer (IMS).
Figure 2:
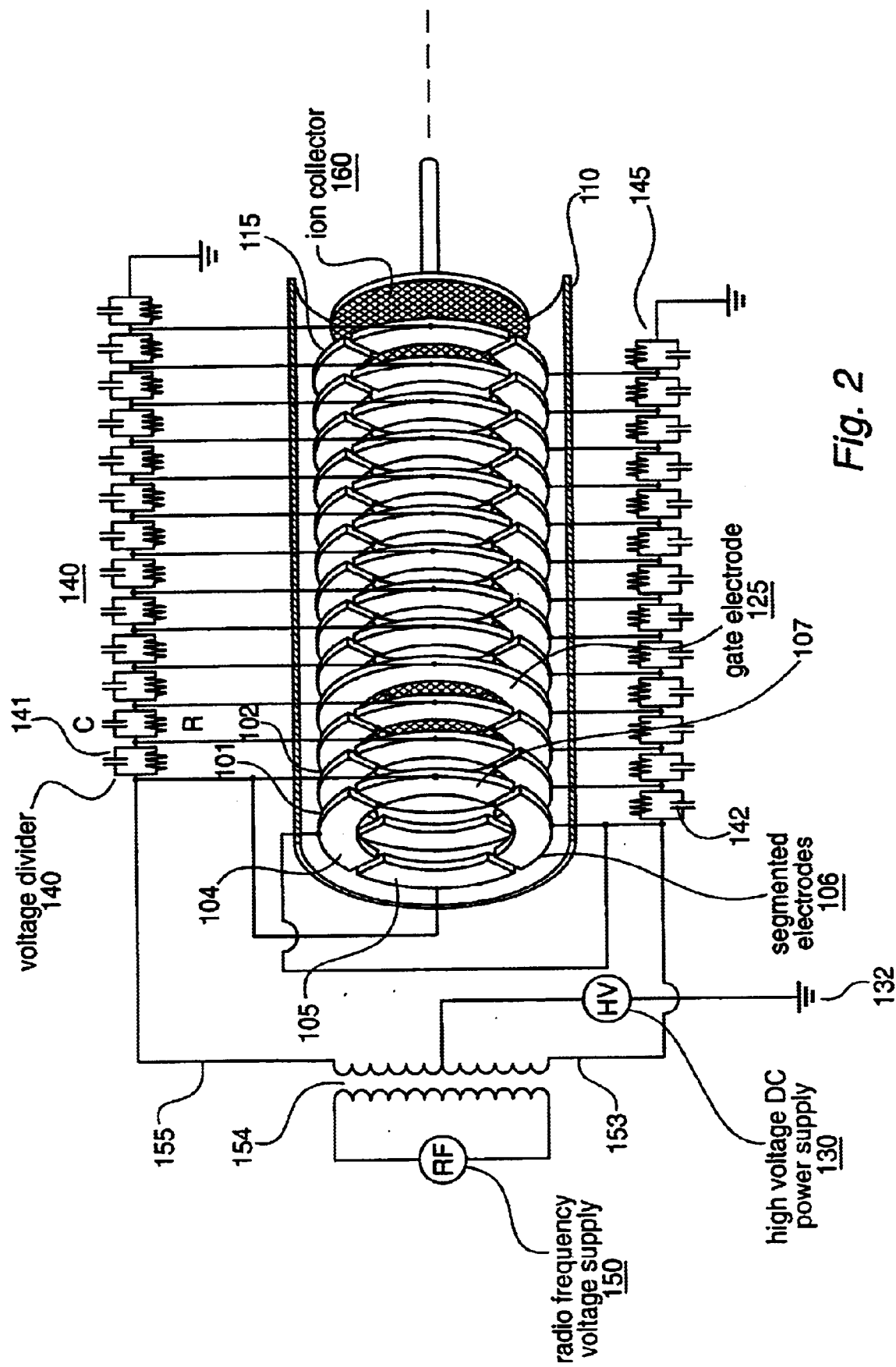
FIG. 2 shows a perspective view of an embodiment of a ring electrode assembly of an ion mobility spectrometer according to the present invention.

Referring to FIG. 2, a perspective view of an IMS drift tube 110 is shown. An stack of ring electrodes (e.g., 101, 102) is axially arranged along the length of the drift tube 110 with the last electrode of the stack adjacent to an ion collector 160 at the end of the tube. Within the stack of electrodes toward the entrance of the drift tube 110, a gate electrode 125 comprising a conductive grid is disposed in the center of one of the ring electrodes. Each individual ring electrode comprises a conductive annulus approximately 0.5 mm to 3 mm in width having an inner diameter that can be chosen depending on the size of the drift tube, but typically ranging between 2 and 40 mm. As shown, each ring electrode (e.g., 101) is radially divided into four separate segments 104, 105, 106, 107 of equal dimensions. The segments 104, 105, 106, 107 can be formed from separate conductive components or can be a structurally integrated component having separate conductive surface segments. Top and bottom segments (e.g., 104, 106) of each ring electrode are connected to a first voltage divider 145, while left and right segments (e.g., 105, 107) are coupled to a second voltage divider 140. The first voltage divider 145 is in turn coupled to a first pole 153 of a transformer 154 connected across a radio frequency (RF) sinusoidal electrical power supply 150, while the second voltage divider 140 is coupled to the second pole 155 of the transformer. It is noted that the waveform of the supplied RF power supply signal can also be non-sinusoidal, such as, e.g., a pulsed square-wave signal, or a sawtooth signal. The main criteria of the power supply signal are a frequency in the RF range, and that the signal have equal parts in positive and negative polarity. The center of the transformer 154 is tapped by a d.c. power supply 130, such that the RF voltage applied via the transformer is offset by the d.c. voltage (U) of the power supply 130.

The first 153 and second 155 poles of the transformer are at opposite potentials, $U+V \cos(\omega t)$ and $U-V \cos(\omega t)$, respectively. The amplitudes U, V of the respective d.c. 130 and RF 150 sources are variable, but are kept under a threshold voltage at which electrical discharges may occur. The frequency $\omega$ of the RF source ranges from about 10 kHz to about 100 MHz. As in conventional IMS systems, the first and second voltage dividers 145, 140 generate a potential gradient along the length of the drift tube, with the first ring electrode at a high positive (for positively charged ions) or low negative d.c. (for negatively charged ions) potential U depending on the charge of the ions. The last ring electrode 115 may be maintained at ground potential, or the first ring electrode may be maintained at ground, in guiding positive and negative ions respectively.

Alternatively, the first and last ring electrodes may be maintained at a non-ground potential. In each case an ion collector 160 is biased accordingly. The voltage dividers 145, 140 comprise resistive segments (e.g., 141) connected in series, with each resistive segment including a resistor and a decoupling capacitor connected in parallel.

In the embodiment shown in FIG. 2, opposite pairs of left and right segments (105, 107) are maintained at $U+V \cos \omega t$ and opposite pairs of top and bottom segments (104, 106) are maintained at $U-V \cos \omega t$. Thus, adjacent segments have equal d.c. potentials and a.c. potentials 180 degrees out of phase with respect to each other. The alternating potentials at the adjacent segments create a quadrupole electric field in the internal region of the ring electrodes. This field acts primarily in the radial direction orthogonal to the axial potential gradient and therefore does not significantly interfere with the potential gradient generated by the d.c. power supply because the axial electric field components of the RF field are minimal relative to the axial field generated by the d.c. source. As known in the art, alternating quadrupole (and other multipole) fields can be used to guide and focus the motion of ions and prevent radial motion out of an axial trajectory. It has been shown that the performance of such ion guides depends upon the amplitude and frequency of the applied RF field, the axial d.c. field, gas pressure and the structural dimensions of the electrodes. While the exact relationship between the various factors is complex and depends upon various experimental conditions, ion trajectory simulations demonstrate that the RF electric fields create an effective radial potential well V* centered on the axis that effectively confines ions along the axis of the rings.

The effective potential V* for a multipole field can be estimated as $$V*(r) = \frac{z|E(r)|^n}{4m\omega^2} \quad (2)$$

where E(r) is the local RF electric field intensity within the inside of the ring electrodes, which has been shown to have a minimum at the central axis of the drift tube at r=0. The exponent n depends on the number of segments. To a first order approximation, n is equal to the number of segments divided by two. Thus quadrupole fields n is 2, for hexapole fields n is 3, etc. This effective potential is similar to those generated in RF only multipole ion guides and likewise acts to constrain transverse motion of the ions and thereby guide the ions along an axial trajectory.

In the context of ion mobility spectroscopy, since ions are differentiated according to their transit time along the axis of the drift tube, all ionic species in a sample must travel the length of the drift tube to be detected. To provide optimal performance of the ion mobility spectrometer shown in FIG. 2, the UN ratio, RF frequency, ring electrode aperture diameter, and ring spacing are accordingly adjusted to transmit the entire expected range of m/z values for the given sample.

The ion mobility spectrometer system shown in FIG. 2 increases ion transmission efficiency to nearly 100% and thus increases instrument sensitivity by two orders of magnitude. Advantageously, the ring electrode assembly is contained within the drift tube and does not add to the length of the drift tube, or add another ion optics stage to the spectrometer, allowing the IMS instrument to retain its normally compact structure.

Although in the embodiment depicted all of the ring electrodes are segmented, in alternative embodiments, only a subset of the ring electrodes are segmented. Depending on the sampling requirements, the radial RF ion containment fields provided by the subset of segmented electrodes may boost the ion transmission efficiency to a great enough extent that further ion containment is unnecessary.

Figure 3B:
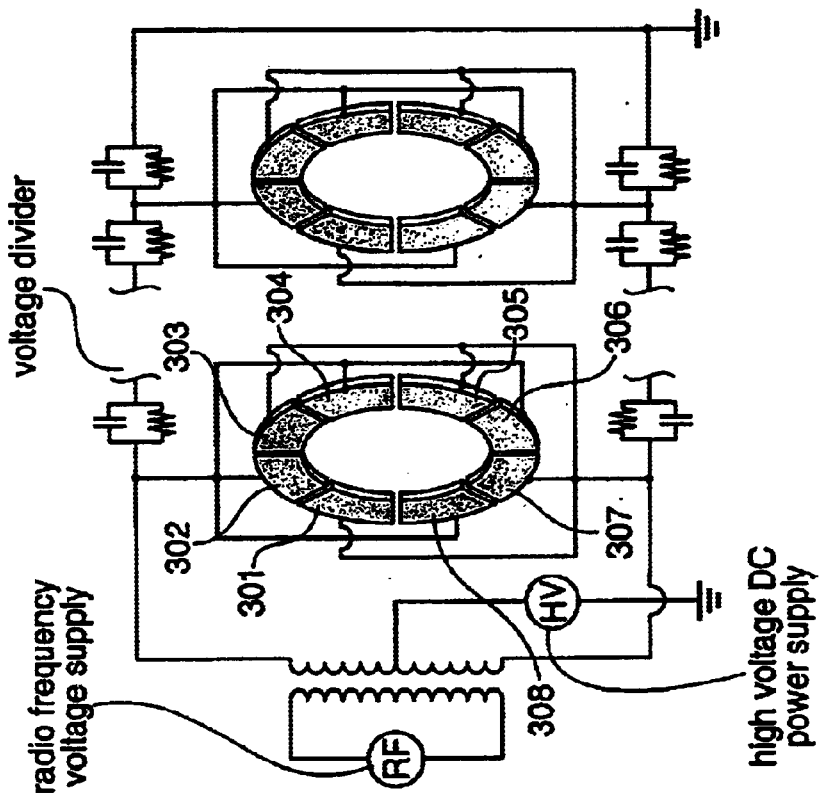
FIG. 3b shows a perspective view of a single ring electrode segmented to generate an octopole field according to the present invention.
Figure 3A:
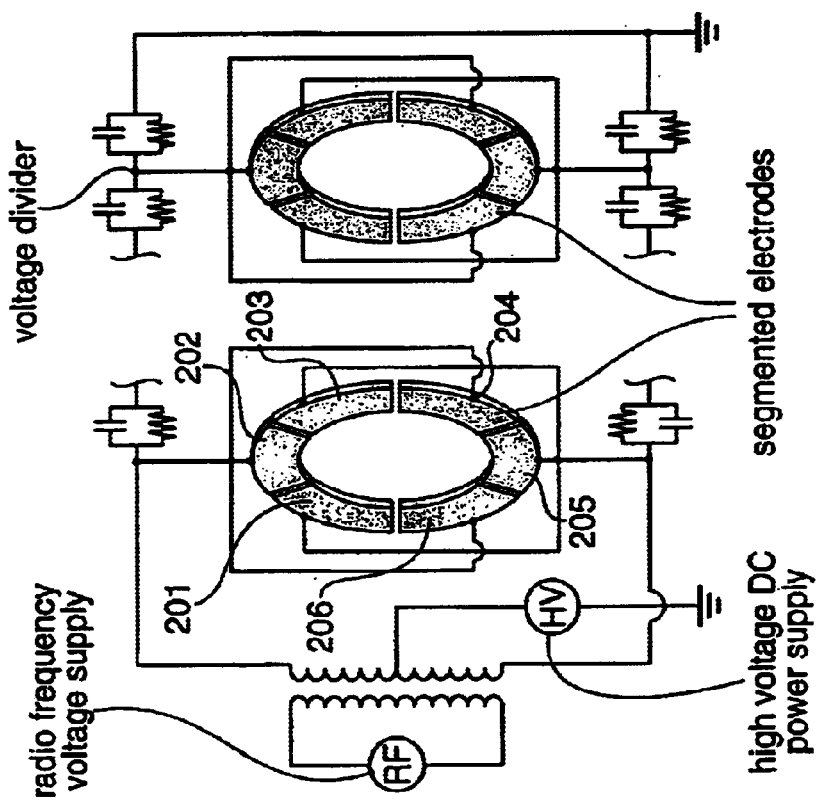
FIG. 3a shows a perspective view of a single ring electrode segmented to generate a hexapole field according to the present invention.

In the alternative embodiment depicted in FIG. 3a, the ring electrodes are divided radially into six equal segments 201, 202, 203, 204, 205, 206. Each segment receives the same d.c. voltage from the d.c. power supply while every other segment, i.e., 201, 203 and 205 receives the same RF voltage from the RF power supply. This segment structure provides for generation of a combination of a linear IMS acceleration field and a RF hexapole field. Similarly, in the alternative embodiment in FIG. 3b, the ring electrodes are divided radially into eight segments 301, 302 . . . 308. with all segments at equal d.c. voltage and every other segment maintained at the same RF voltage. In this embodiment, the segment structure produces a combination of a linear IMS acceleration field and an RF octopole field. The number of segments of the ring electrodes is not limited, as long as the number of segments is even, the dimensions of the segments are equivalent, and the distribution of the segments is symmetric. In this regard, higher order fields such as decapole (10 segments) or dodecapole fields (12 segments) can be implemented.

Figure 4:
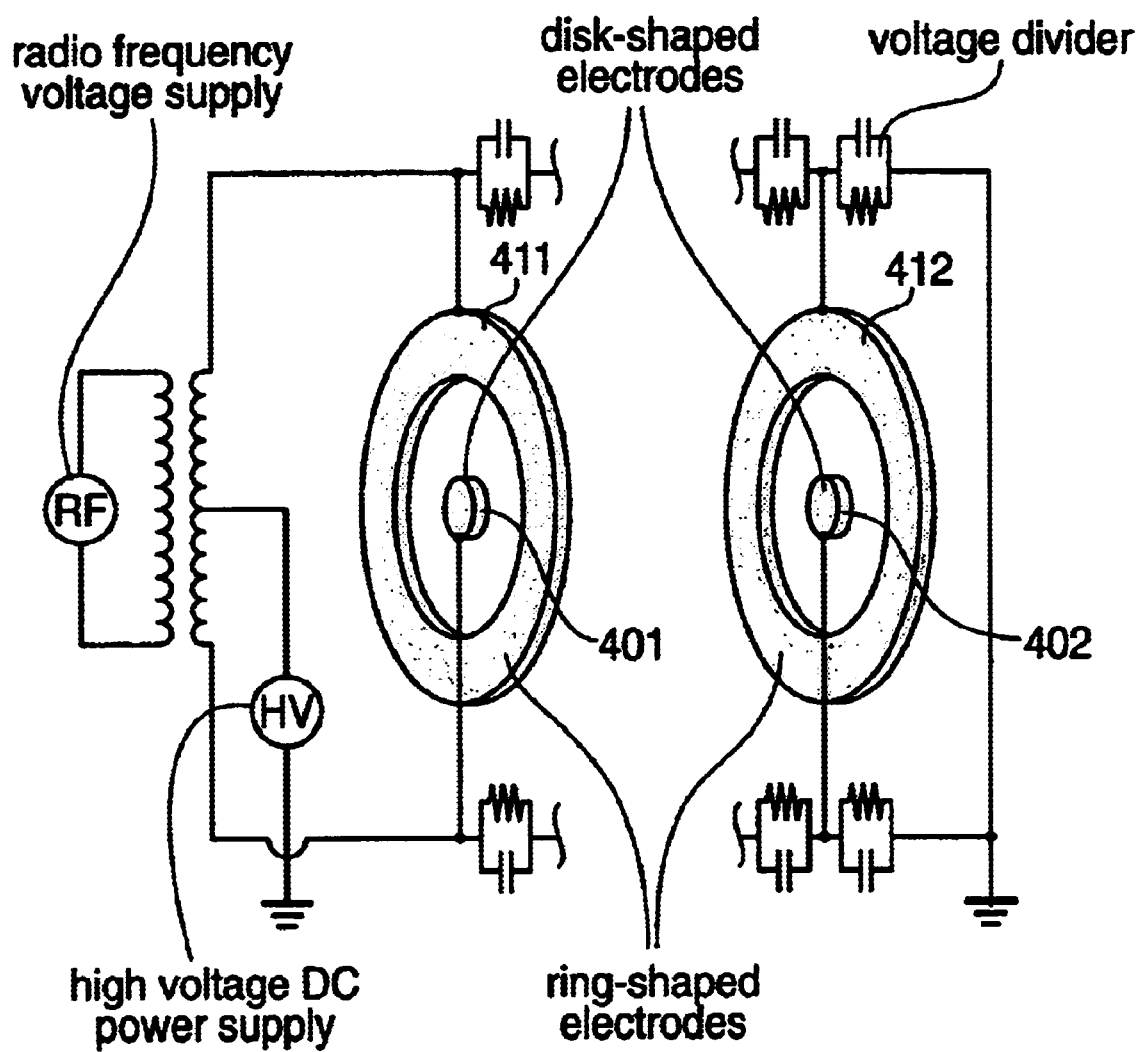
FIG. 4 shows a schematic perspective view of an alternative embodiment of the ring electrode assembly according to the present invention wherein disks are disposed in the center of the ring electrodes to provide a radial field.

While the segmented ring electrode structure provides for quadrupole and higher order RF fields, alternative structures can be used to provide radial ion containment fields in the context of IMS systems. FIG. 4 schematically illustrates an alternative structure in which disk-shaped electrodes 401, 402 are placed in the geometric center of the ring electrodes 411, 412, aligned in the axial direction. Each of the disk electrodes 401, 402 has a diameter substantially smaller than the inner diameter of the ring electrodes 411, 412. The disk electrodes 401, 402 along the axis of the drift tube are maintained at the same d.c. voltage as the respective ring electrodes 411, 412 at the same axial location, while an oscillating RF field is generated between the respective disks and ring electrodes. This radial field can normally be approximated as a dipole field that constrains ions within the annular region between the disks 401, 402 and the ring electrodes 411, 412. As has been shown in applications of field assymetric waveform ion mobility spectroscopy (FAIMS), atmospheric pressure dipole RF fields can be used to separate ions of different mobility in the area of field assymetric waveform ion. See, e.g., Buryakov et al., International Journal of Mass Spectroscopy Ionn. Proc. 128. p. 143, 1993.

FIG. 5 is a perspective view depicting an embodiment for mounting the disk-shaped electrodes along the axis of an ion mobility spectrometer. In FIG. 5, disk electrodes such as 505, 506, 507 are attached to disk-shaped insulators e.g., 511, 512, which act as spacers between the disk-shaped electrodes. The electrodes 505, 506, 507 can be attached to insulators 511, 512 by chemical and mechanical means including, but not limited to, glueing with an adhesive binding, and mechanically fitting or fastening. The disk-shaped insulators may have the same diameter as the disk-shaped electrodes and may be made from an insulating material such as Teflon, Vespel, etc. Similarly, the outer ring electrodes 515, 516, 517 are attached to and equally spaced by a series of ring-shaped insulators such as 521, 522 which have radial dimensions that match the ring electrodes. One or more of the disk shaped insulators 511, 512 are coupled to the ring-shaped insulators by a number of insulating radial spokes 531, 532 for structural support. As shown in cross-sectional views taken along an insulating spacer in FIGS. 6A, 6B and 6C, the number of spokes connecting a particular disk-shaped insulator to a ring-shaped insulator can vary, and one (as in FIG. 6A), two (as in FIG. 6B), or three (as in FIG. 6C) spokes can be used. Moreover as depicted in FIGS. 6A, 6B and 6C, the disk, spokes and ring can be integrated into single insulator structures 550a, 550b, 550c by means of molding or machining a workpiece.

Figure 7:
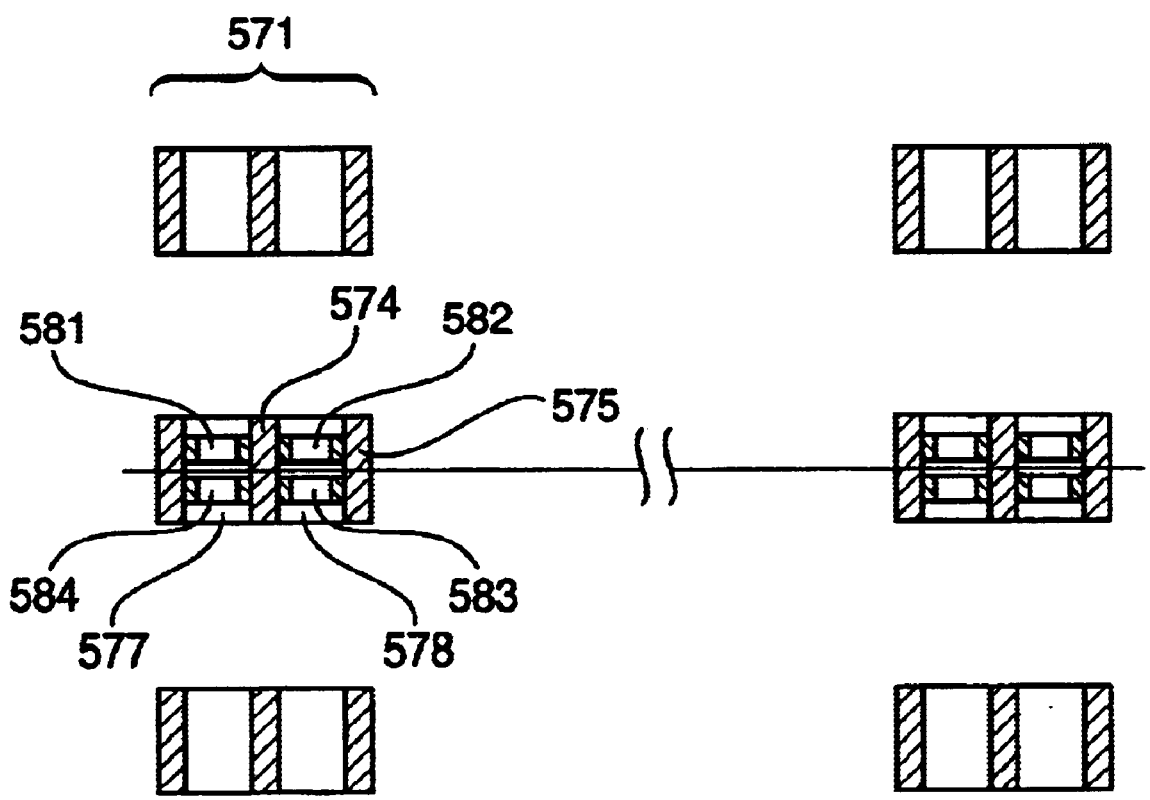
FIG. 7 depicts a cross-section along the axis of the ion mobility spectrometer and shows two axially separate groups of ring electrodes and disk electrodes having internal electrical connections.

FIG. 7 depicts a cross-section along the axis of the ion mobility spectrometer and shows two axially separate groups of ring electrodes and disk-shaped electrodes separated by insulators. To establish electrical connections to the disk-shaped electrodes 573, 574, 575 shown in group 571, connections to the resistor capacitor chain of the voltage divider may be embedded directly into the insulators 577, 578 between the disk-shaped electrodes. In an exemplary configuration, surface mount resistors 581, 582 and surface mount capacitors 583, 584 are sandwiched between and in electrical contact with the disk-shaped electrodes 573, 574, 575.

In the foregoing description, the invention has been described with reference to a number of examples that are not to be considered limiting. Rather, it is to be understood and expected that variations in the principles of the method and system herein disclosed may be made by one skilled in the art and it is intended that such modifications, changes, and/or substitutions are to be included within the scope of the present invention as set forth in the appended claims. For example, additional configurations for generating oscillating radial fields within IMS ring electrodes are fully consistent with the premises of the invention described herein.

What is claimed is:

1. An ion mobility spectrometer comprising:
    a drift tube in said ion mobility spectrometer having a central axis and first and second ends;
    an ion source for directing ions into the first end of the drift tube;
    a plurality of ring electrodes arranged along the central axis of the drift tube providing a linear potential gradient along the central axis of the drift tube, each having an internal region defining a radial space perpendicular to the central axis of the drift tube; and
    an RF voltage source coupled to the plurality of ring electrodes and generating an oscillating RF potential within the internal region of each of the ring electrodes, the oscillating RF potential influencing radial motion of the ions within the drift tube so that the ions remain within the radial spaces defined by the internal regions of the electrodes while moving axially to the second end of the drift tube.

2. The ion mobility spectrometer of claim 1, wherein one or more of the plurality of ring electrodes are segmented and include an even number of segments, each segment being electrically insulated from and having an opposite polarity RF potential from adjacent segments, thereby generating a multipole field within the respective internal region of the segmented ring electrodes.

3. The ion mobility spectrometer of claim 2, wherein each of the plurality of segmented ring electrodes includes four segments.

4. The ion mobility spectrometer of claim 2, wherein each of the plurality of ring electrodes includes either six segments or eight segments.

5. An ion mobility spectrometer of claim 1, further comprising:
    a plurality of disk electrodes, one of the plurality of disk electrodes coaxial with and centered in the internal region of each of the plurality of ring electrodes;
    wherein an RF voltage source is coupled to each of the plurality of disk electrodes such that an oscillating RF potential is generated between each of the plurality of ring electrodes and the respective coaxial disk electrodes.

6. The ion mobility spectrometer of claim 1, wherein the drift tube includes a drift gas maintained at approximately atmospheric pressure.

7. The ion mobility spectrometer of claim 1, wherein the oscillating RF potential has a frequency in the range of 500 kHz to 10 MHz.

8. An ion mobility spectrometer comprising:
    a drift tube in said ion mobility spectrometer having a central axis and first and second ends;
    an ion source for directing ions into the first end of the drift tube;
    a plurality of ring electrodes arranged along the central axis of the drift tube providing a linear potential gradient along the central axis of the drift tube and each having an internal region defining a radial space perpendicular to the central axis of the drift tube, a subset of the plurality of ring electrodes being segmented; and
    an RF voltage source coupled to the subset of segmented ring electrodes and generating an oscillating RF potential within the internal region of each of the subset of segmented ring electrodes, the oscillating RF potential influencing radial motion of the ions within the drift tube so that the ions remain within the radial spaces defined by the internal regions of the plurality of ring electrodes while moving axially to the second end of the drift tube.

9. The ion mobility spectrometer of claim 8, wherein each of the subset of segmented ring electrodes includes an even number of segments, each segment being electrically insulated from and having an opposite RF potential of opposite polarity to the adjacent segments, thereby generating a multipole field within the respective internal region of each of the subset of ring electrodes.

10. An arrangement for efficiently differentiating between ionic species according to ionic mobility at atmospheric pressure, comprising:
    a tube having a central axis, a first end for receiving ions and a second end;
    a plurality of segmented ring electrodes arranged along the central axis of the tube providing a linear potential gradient along the central axis of the drift tube, each having an internal region; and
    an RF voltage source coupled to the plurality of segmented ring electrodes and generating an oscillating RF potential within the internal region of each of the segmented ring electrodes;
    wherein the oscillating RF potential constrains radial motion of the ions within the tube so that the ions remain within the internal regions of the ring electrodes and the linear potential gradient influences the ions to move axially from the first end to the second end of the tube.

11. The arrangement of claim 10, wherein each of the plurality of segmented ring electrodes includes an even number of segments, each segment being electrically insulated from and have an opposite polarity RF potential from adjacent segments, thereby generating a multipole field within the respective internal region of each of the segmented ring electrodes.

12. The arrangement of claim 11, wherein each of the plurality of ring electrodes includes four segments.

13. The arrangement of claim 11, wherein each of the plurality of ring electrodes includes either six segments or eight segments.

14. An arrangement for efficiently differentiating between ionic species according to ionic mobility at atmospheric pressure, comprising:
    a tube having a central axis, a first end for receiving ions and a second end;
    a plurality of ring electrodes arranged along the central axis of the tube providing a linear potential gradient along the central axis of the drift tube, each having an internal region;
    a plurality of disk electrodes, each situated at a center of the internal region each one of one of the plurality of ring electrodes; and
    an RF voltage source coupled to each of the plurality of disk electrodes such that an oscillating RF potential is generated between each of the plurality of ring electrodes and the respective disk electrode centered at each ring electrode.

15. An arrangement for efficiently transmitting ions in a linear direction, comprising:
    a tube having a central axis, a first end for receiving ions and a second end;

a plurality of ring electrodes having respective internal regions arranged along the central axis of the tube providing a linear potential gradient along the central axis of the drift tube, a subset of the plurality of ring electrodes being segmented; and the RF voltage source coupled to the subset of the plurality of ring electrodes, the RF voltage source generating an oscillating RF potential within the internal region of each of the subset of ring electrodes;

wherein the oscillating RF potential constrains radial motion of the ions within the tube so that the ions remain within the internal regions of the plurality of ring electrodes and the linear potential gradient influences the ions to move axially from the first end to the second end of the tube.

16. The arrangement of claim 15, wherein each of the subset of ring electrodes includes an even number of segments electrically insulated from and having RF potential of opposite polarity from adjacent segments, thereby generating a multipole field within the respective internal region of each of the subset of ring electrodes.

17. A method for efficiently transmitting ions along a central axis of a stack of electrodes in an ion mobility spectrometer, the method comprising:

introducing ions along the axis in said ion mobility spectrometer;

directing the ions along the axis with a DC electric field; and constraining ion motion perpendicular to the axis with a radial RF electric field.

18. The method of claim 17, further comprising the step of:

applying an oscillating potential to a set of said electrodes, thereby creating the radial RF electric field.

19. The method of claim 18, wherein the electrodes are segmented.

20. The method of claim 19, wherein the step of applying comprises applying said oscillating potential between adjacent segments of each electrode of said set of electrodes, thereby creating a radial RF multipole electric field.

21. The method of claim 18, wherein the step of applying comprises applying said oscillating potential between each electrode of said set of electrodes and a disk electrode centered on said axis.

22. A method for efficiently transmitting ions along a central axis of a stack of segmented electrodes in an ion mobility spectrometer, the method comprising:

introducing ions along the axis in said ion mobility spectrometer;

directing the ions along the axis with a DC electric field; and constraining ion motion perpendicular to the axis with a radial RF multipole electric field.

23. The method of claim 17, further comprising the step of:

applying an oscillating potential to a set of said segmented electrodes, thereby creating the radial RF multipole electric field.

24. The method of claim 19, wherein the step of applying comprises applying said oscillating potential between adjacent segments of each electrode of said set of electrodes, thereby creating a radial RF multipole electric field.

25. The method of claim 24, wherein the number of segments per electrode is one of four, six and eight.

* * * * *